United States Patent [19]
Friese

[11] 3,970,712
[45] July 20, 1976

[54] HYDROLYSIS OF OAT HUSKS

[75] Inventor: Hermann Friese, Berlin, Germany

[73] Assignee: Sud-Chemie AG, Munich, Germany

[22] Filed: Nov. 13, 1974

[21] Appl. No.: 523,456

[30] Foreign Application Priority Data

Nov. 23, 1973 Germany .......... 2358472

[52] U.S. Cl. .......... 260/635 C; 127/37; 260/124 R; 260/124 A

[51] Int. Cl.[2] .......... C07C 29/00; C07G 1/00; C13K 1/02; C13K 13/00

[58] Field of Search .......... 260/124 R, 124 A, 635 C

[56] References Cited

UNITED STATES PATENTS

| | | | |
|---|---|---|---|
| 2,615,883 | 10/1952 | Sweeney | 127/37 |
| 2,801,955 | 8/1957 | Rutenberg | 127/37 X |
| 2,835,611 | 5/1958 | Snyder | 127/37 |
| 3,212,933 | 10/1965 | Hess | 127/37 |
| 3,251,716 | 5/1966 | Porter | 127/37 |
| 3,565,687 | 2/1971 | Suminoe | 127/37 |
| 3,579,380 | 5/1971 | Friese | 127/37 |
| 3,784,408 | 1/1974 | Jaffe | 127/37 |
| 3,787,241 | 1/1974 | Eickemeyer | 127/37 |
| 3,817,826 | 6/1974 | Nygard | 260/124 A |

*Primary Examiner*—Morris O. Wolk
*Assistant Examiner*—Sidney Marantz
*Attorney, Agent, or Firm*—Watson Leavenworth Kelton & Taggart

[57] ABSTRACT

A process for the hydrolysis of oat husks is carried out with alkali metal hydroxide or alkali metal chlorite in a first stage and with mineral acid in a second stage to provide D-(+)-xylose. The xylose can be recovered as such, or converted in situ to xylitol. The solid residue by-product of the aforesaid process for the hydrolysis of oat husks, following removal of the lignin content thereof, is readily convertible to cellulose.

31 Claims, No Drawings

HYDROLYSIS OF OAT HUSKS

BACKGROUND OF THE INVENTION

1. Field of the Invention

This invention relates to methods for hydrolyzing oat husks to provide D-(+)-xylose, and through subsequent treatment, if desired, xylitol, lignin and cellulose.

2. Description of the Prior Art

D-(+)-xylose and its hydrogenation product, xylitol, are of considerable industrial significance. For example, xylose can be employed for various purposes in the foodstuffs industry, while xylitol has proved to be a very good sweetener for diabetics. Varieties of deciduous timber, such as beech and chestnut, are used almost exclusively as the starting material for the industrial manufacture of xylose. The yields are about 10–12% (compare, for example, German Pat. No. 912,440). It is a significant disadvantage of these processes that the wood material which remains, so-called cellolignin, has hitherto been incapable of practicable industrial utilization and that the process mentioned only gives moderate yields of xylose.

German Pat. No. 834,079 has disclosed the production of xylose from oat husks. Oat husks contain about 38% of pentosan while, for example, beechwood and birchwood only contain 24–25% and maize cobs contain about 28% of pentosans. In this process the oat husks are heated to boiling with 0.08% strength ammonia or are extracted with benzene/alcohol. Thereafter, the usual hydrolysis under pressure is carried out with 0.2 to 0.5 % strength $H_2SO_4$ at 125°C. Further working up is not carried out. In the pretreatment with $NH_3$, 4 kg of $NH_3$, as an 0.08% strength solution, are used per 1,000 kg of oat husks. However, 17 kg of $NH_3$ would be necessary to split off the acetic acid. Furthermore, under the conditions mentioned in German Pat. No. 834,079, it is likely that hardly any splitting off, and hence removal, of the acetic acid, which accounts for approximately 6% of the weight of the oat husks, takes place.

There is therefore a need for a process which, firstly, permits complete utilization of the starting material, and secondly, gives a higher yield of xylose so that the process is economical.

SUMMARY OF THE INVENTION

The subject of the present invention is a process for the hydrolysis of oat husks to provide D-(+)-xylose which is characterized in that the hydrolysis is carried out with alkali metal hydroxide or alkali metal chlorite in a first stage and with a mineral acid in a second stage. The xylose can be recovered as such or converted in situ to xylitol. The solid residue by-product of the aforesaid process for the hydrolysis of oat husks, following removal of the lignin content thereof, is readily convertible to cellulose.

As a result of the use of alkali metal hydroxide or alkali metal chlorite in the first process stage of the process according to the invention, the (chemically) bonded acetic acid present in the oat husks is split off. In addition, the crystallization-inhibiting nitrogen-containing substances and other concomitant substances, about the nature of which nothing is known as yet, go into solution, while the pentosan is not attacked by the alkali metal hydroxide or alkali metal chlorite. The acetic acid can be distilled off and can, if desired, be isolated from the distillate by extraction with a suitable solvent.

DESCRIPTION OF THE PREFERRED EMBODIMENTS

If alkali metal hydroxide is used in the first stage, then sodium hydroxide and potassium hydroxide, but especially sodium hydroxide, are preferred. The process can be carried out, for example, in aqueous solution. When working under normal pressure, the concentration of the alkali metal hydroxide can be, for example, 0.6–4% by weight, based on solvent and alkali metal hydroxide. The preferred concentration range is 0.6–3, in particular, 1–2% by weight. The temperature is 15–100°C, preferably, 25°–60°C.

By way of example, 1.2% strength aqueous NaOH at room temperature dissolves almost 20% of the oat husk material, the acetic acid is split off and the residue contains 50.5% of pentosan. 2% strength NaOh at 50°C dissolves 38% of the oat husk material and the residue contains 46.6% of pentosan; 3% strength NaOh at 50°C dissolves 40% of oat husk material and the residue contains 31% of pentosan; 4% strength NaOH at 60°C. dissolves about 45% of oat husk material and the residue contains 30% of pentosan.

If the process is carried out under pressure it is possible to use, for example, alkali metal hydroxide concentrations of 0.3 to 1.5% by weight, preferably of between 0.5 and 1.0% by weight. In that case, the most advantageous concentration is 0.66% by weight. The pressure is preferably up to 3 atmospheres gauge and the temperature is preferably up to 125°C. The pressure is in general generated autogenically in the autoclave. If the process is carried out under pressure with 0.66% strength NaOH, 25–27% of the interfering materials are dissolved and the residue contains 50% of pentosan.

If the hydrolysis in the first stage of the process according to the invention is carried out with alkali metal chlorite, the potassium salt or sodium salt, but especially the sodium salt, is again used for preference. The concentration of the chlorite in the solvent, which is preferably water, is up to 10% by weight, 2 to 6% by weight being preferred. The pH value of the reaction mixture is initially adjusted to be alkaline, preferably at least 11. Thus, in contrast to the usual reactions with alkali metal chlorite, the treatment is not carried at an acid pH value already from the start. During the hydrolysis, the pH value drops to about 4–5. The process is carried out without use of pressure and the temperature is preferably between 15° and 60°, especially between 30° and 55°C. The oat husks lose approximately 11% of their weight and have a white-yellowish appearance, the acetic acid has been split off and the pentosan content of the residue has risen to 49.8%. Since the amount of $NaClO_2$ consumed is only as much as corresponds to the acetic acid split off, the reaction solution can be reused several times after replacing the $NaClO_2$ consumed, which must always be present in exess.

After removing the acetic acid by filtration, the oat husks treated in the first stage are hydrolyzed, in a manner which is in itself known, with a dilute mineral acid at elevated temperatures with or without use of pressure.

This process can be carried out, for example, with $H_2SO_4$, HCl or HBr, for example, in water, but preferably with $H_2SO_4$. When working without pressure, preferably 1.5–6.0% strength by weight HCl or HBr or 1.5–6.0 % strength by volume $H_2SO_4$ and a liquid to solid ratio of 3–6 parts by volume is used. An elevated temperature, preferably 50°–125°C is employed, and in that case, about 2 to 4 hours are required for the second stage of the process according to the invention.

When working under pressure, a pressure of up to 4 atmospheres gauge, in particular 1–3 atmospheres gauge, is used preferentially, and the temperature is preferably 125°–135°C. The acid concentration is preferably 0.2–0.6% by weight HCl or HBr or 0.2–0.6% by volume of $H_2SO_4$ and the ratio of liquid to solid should preferably be from 4:1 to 7:1 volumes/weight of solids. The time required is approximately 1–2 hours.

After completion of the second stage of the process, the batch is filtered. The liquid can be processed to give xylose or directly to give xylitol. If sulphuric acid has been used in the second stage, the mixture can be neutralized with calcium oxide, calcium carbonate or, preferably, barium carbonate, in the calculated amount. In that case, after removing the precipitate, a xylose solution which can be reduced directly to xylitol, is obtained, while hitherto it has been necessary to concentrate the solution or pass it over ion exchangers to remove acetic acid. The yield of pure xylose is up to 25% and further proportions of xylose, namely up to 10%, can be isolated from the mother liquor.

The process according to the invention results in splitting of the bonds of the lignin to the polysaccharides in the oat husks, without the lignin undergoing a further polymerization, as is the case in the known hydrolysis processes. The lignin can easily be dissolved out of the filtration residue from the second stage of the process according to the invention, by washing with an organic solvent such as methanol or acetone, temperatures of 10°C up to the boiling point of the solvent being suitable. As much as 90% of the lignin is dissolved out at room temperature. The lignin is then obtained as a yellowish-brownish powder which is also dissolved by various other solvents. The substance is thermoplastic and very reactive and is used as the base material for industrially utilizable products, such as dyestuffs and pesticides. Yet further amounts of lignin can be dissolved by treatment with methanol under pressure.

Suprisingly, the residue remaining after the methanol treatment can be hydrolyzed to an almost white cellulose even at waterbath temperature (approximately 88° to 95°C) using dilute alkali metal hydroxide solution, preferably NaOH, for example using 1–4% strength NaOH, while in other circumstances boiling under pressure at up to 180°C is necessary. The cellulose is obtained in a yield of approximately 70% and can be obtained in a pure white form by brief customary bleaching.

The residue can also be treated with alkali and $H_2O_2$ instead of with alkali.

A third embodiment is to treat the residue with dilute alkali metal chlorite solution, especially with sodium chlorite solution. Here, in contrast to the known processes which are carried out in the acid range, an alkali chlorite solution which has been adjusted to a basic pH value, especially to a pH value of at least 11, is employed. In this way, the residue is very easily hydrolyzed, giving pure white finely fibrous cellulose in a yield of approximately 85%. This cellulose can easily be pulverized and can, inter alia, be used as so-called foodstuff-grade cellulose.

EXAMPLE 1

1 kg of oat husks are left to stand with 4 l of 1.2% strength NaOH solution for 24 hours at room temperature, with frequent shaking and mechanical working, and while following the decreasing titre of the solution. The mixture is then suction-filtered and the residue is well washed with $H_2O$ until the solution which passes through, and which is initially turbid, has become clear. A determination of the residue shows 50.5% of xylose (pentosan content conversion by calculation, to the pentose). The residue is furthermore now free from nitrogen.

The filtrate is acidified with sulphuric acid and the acetic acid from the distillate is determined; it is found that the oat husks contain from 5.8 to 6% of acetic acid.

1.2 l of 3% strength by volume $H_2SO_4$ are added to 300 g (calculated as solids) of the residue, the liquid being completely absorbed. Thereafter, the mixture is heated in an oil bath for 2 hours to 120°–125°C under reflux, and in the course thereof soon becomes mobile. After suction filtration and thorough pressing-out, the residue is rinsed with water; the filtrate is brown-yellow and on standing some sediment forms, and for this reason the filtrate is clarified with kieselguhr and decolorized with active charcoal and the solution, which retains a greenish-yellowish tinge, is neutralized with the calculated amount of $BaCO_3$ and concentrated in vacuo at 45°C until it is slightly syrupy. After seeding and standing in the cold, crystallization occurs. The cyrstals are filtered off and briefly washed with 85% strength methanol. Pure xylose is obtained in a yield of 75.5 g. Further proportions are isolated in an amount of approximately 15 g, from the mother liquor by fractionation with methanol and isopropanol.

The mother liquor which thus remains is still a mixture of D-xylose, L-arabinose and glucose, which is difficult to separate.

As was to be expected, the distillate contains no further acetic acid.

To ascertain what amounts of xylose were converted to furfuraldehyde during the hydrolysis process, a determination of the distillate is carried out with 2,4-dinitrophenylhydrazine; this shows that about 1.5% of the xylose produced has reacted further to give furfuraldehyde.

The hydrolysis residue is washed with methanol until the latter becomes colorless, and then weighs 160.1 g and still contains 12.1% of pentosan, so that approximately 124 g of this substance have passed into the hydrolysis liquid. The brown-yellow methanol filtrate, which still contains $H_2O$ from the moist hydrolysis residue, is evaporated, in the course of which the lignin precipitates after the methanol has evaporated, and is filtered off. The aqueous filtrate still contains residual xylose and can be worked up.

To isolate cellulose, 150 g of this residue are left to stand, without acidification, with 20–50 g of 80% strength sodium chlorite dissolved in 1.4 l of $H_2O$. After some time, the mass swells up and loss of color occurs. The substance is then stirred at approximately 40°C until it has become light in color. It is then filtered off, washed with $H_2O$ until the odor of $ClO_2$ has disappeared, and dried.

A pure white flocculent substance, which is very easy to grind, remains in a yield of almost 90%.

A further 100 g of the hydrolysis residue treated with methanol are warmed with 700 ccs of 2% strength NaOH for 2 hours on a waterbath at approximately 95°C, filtered off on a glass frit and rinsed with $H_2O$ until the initially dark brown filtrate has become colourless. The remnants of alkali are removed with 1 % strength acetic acid.

Here again, a flocculent, slightly brownish-colored cellulose is produced, which is immediately turned white by a customary bleaching agent. The yield is 70% since the alkali metal hydroxide solution also dissolves out pentosan constituents which are still present, which is not the case using hydrolysis with $NaClO_2$.

EXAMPLE 2

1 kg of oat husks and 6 l of 0.66 % strength NaOH (40 g) are heated to 125°C over the course of 40 minutes at 0.9 to 1.3 atmospheres gauge and then allowed to cool, and the solids are filtered off, using a fiber fleece, and are washed well. The residue amounts to approximately 750 g and contains 48.5% of pentosan.

If the oat husks are heated in the autoclave under the same conditions, but only to 105°C, a residue of 876 g, containing approximately 43% of pentosan, is obtained.

600 g of this residue, 4 l of $H_2O$ and 24 ccs of concentrated $H_2SO_4$ are heated for 90 minutes to 134°C in a stirred autoclave, stirring being readily possible from 70°C upwards. After filtration, washing with $H_2O$ and treatment with methanol, the residue amounts to 283.7 g and only retains 8.1 % of pentosan.

The acid filtrate is neutralized with the calculated amount of $BaCO_3$ while stirring, and is clarified with active charcoal. After evaporation under reduced pressure at 45°C until slightly syrupy, approximately 25% of pure xylose crystals can be isolated; a further 6% can be obtained from the mother liquor.

100 g of the hydrolysis residue treated with methanol are stirred with 1 l of 1.2% strength NaOH for 1 hour at 90/92°C on a waterbath, and after being left to stand overnight, the mixture is filtered through a glass frit. The residue is washed with hot water until the alkalinity has disappeared, and is dried. It consists of white cellulose, the methoxy content of which is about 0.5 to 0.6%. The yield is about 73 g.

EXAMPLE 3

100 g of oat glumes are mixed with a solution of 30 g of $NaClO_2$ in 500 ccs of $H_2O$; the pH value is 11. The mixture is warmed to 50°C for 2 hours on a waterbath, while stirring; in the course of this, the pH value drops to 4 and the color of the reaction mixture changes from brownish to yellow. The acetic acid is split off and liberates $ClO_2$, which then reacts further. After cooling, the mixture is filtered and the residue is well rinsed with water. The yield is about 89 g, and the material contains approximately 49.1 % of pentosan and 2.5% of $OCH_3$ groups. The materials containing nitrogen have been removed.

I claim:

1. A process for the hydrolysis of oat husks which comprises:

a. hydrolyzing oat husks with a solvent containing at least one member selected from the group consisting of alkali metal hydroxide and alkali metal chlorite to provide oat husks from which the chemically bound acetic acid originally present therein has been substantially completely removed, and a solution of acetic acid;

b. recovering the oat husks from which the chemically bound acetic acid has been substantially removed; and c. hydrolyzing the oat husks of step (b) with a mineral acid to provide a solid residue containing lignin and an acidic solution of D-(+)-xylose.

2. The process of claim 1 wherein the solid residue containing lignin is separated from the acidic solution of D-(+)-xylose, the residue is extracted with organic solvent to remove the lignin therefrom and the remaining residue is treated with at least one member of the group consisting of alkali metal chlorite and alkali metal hydroxide at elevated temperature.

3. The process of claim 1 wherein the D-(+)-xylose present in the acid solution of step (c) is recovered therefrom in substantially pure form.

4. The process of claim 1 wherein the acid employed in hydrolysis step (c) is sulphuric acid, the acidic solution of D-(+)-xylose is neutralized with base and the xylose is thereafter reduced in situ to provide xylitol.

5. The process of claim 4 wherein the xylitol is recovered from solution in substantially pure form.

6. The process of claim 2 wherein the lignin is recovered from the extract solution thereof in substantially pure form.

7. The process of claim 1 wherein hydrolysis step (a) is carried out with a solution of sodium hydroxide, potassium hydroxide or combination thereof.

8. The process of claim 7 wherein the solution is an aqueous solution.

9. The process of claim 7 wherein hydrolysis step (a) is carried out under ambient pressure with an alkali metal hydroxide concentration of 0.6 to 4% by weight based on solvent and alkali metal hydroxide.

10. The process of claim 9 wherein the alkali metal hydroxide concentration is 1 to 2% by weight based on solvent and alkali metal hydroxide.

11. The process of claim 9 wherein a temperature of 15° to 100°C. is employed in hydrolysis step (a).

12. The process of claim 11 wherein a temperature of 20° to 60°C. is employed in hydrolysis step (a).

13. The process of claim 7 wherein hydrolysis step (a) is carried out under elevated pressure with an alkali metal hydroxide concentration of 0.3 to 1.5 % by weight based on alkali metal hydroxide and solvent.

14. The process of claim 13 wherein the alkali metal hydroxide concentration is 0.5 to 1% by weight based on solvent and alkali metal hydroxide.

15. The process of claim 13 wherein hydrolysis step (a) is carried out at a pressure up to 3 atmospheres gauge and at a temperature up to 125°C.

16. The process of claim 1 wherein hydrolysis step (a) is carried out at ambient pressure with a solution of sodium chlorite, potassium chlorite or mixture thereof.

17. The process of claim 16 wherein the solution of sodium chlorite, potassium chlorite or mixture thereof is an aqueous solution.

18. The process of claim 16 wherein an alkali metal chlorite concentration of up to 10% by weight based on solvent and alkali metal chlorite is employed.

19. The process of claim 18 wherein an alkali metal chlorite concentration of from 2 to 6% by weight based on solvent and alkali metal chlorite is employed.

20. The process of claim 16 wherein the pH value of the solution of sodium chlorite, potassium chlorite or mixture thereof is initially adjusted to be alkaline.

21. The process of claim 20 wherein the pH value is initially adjusted to at least 11.

22. The process of claim 16 wherein hydrolysis step (a) is carried out at a temperature of 15° to 60°C.

23. The process of claim 22 wherein hydrolysis step (a) is carried out at a temperature of 30° to 55°C.

24. The process of claim 2 wherein the lignin containing residue is extracted with methanol.

25. The process of claim 2 wherein the step of treating the residue from which the lignin has been removed is carried out with alkali metal chlorite at a basic pH or with alkali metal hydroxide in the presence or absence of hydrogen peroxide.

26. The process of claim 25 wherein aqueous alkali metal hydroxide is employed.

27. The process of claim 25 wherein the alkali metal hydroxide is sodium hydroxide.

28. The process of claim 26 wherein 1 to 4% aqueous alkali metal hydroxide solution is employed.

29. The process of claim 26 carried out at 88° to 95°C.

30. The process of claim 25 wherein the residue from which the lignin has been removed is treated with alkali metal chlorite at a pH of at least 11.

31. The process of claim 2 wherein the residue from which the lignin has been extracted is treated in the presence of hydrogen peroxide with at least one member of the group consisting of alkali metal chlorite and alkali metal chloride at elevated temperature.

* * * * *